United States Patent [19]

Shonk

[11] Patent Number: 5,304,135
[45] Date of Patent: Apr. 19, 1994

[54] AXIAL MULTI-CHAMBER ANGIOPLASTY BALLOON ASSEMBLY

[75] Inventor: Robert S. Shonk, Davie, Fla.

[73] Assignee: Cordis Corporation, Miami Lakes, Fla.

[21] Appl. No.: 929,092

[22] Filed: Aug. 13, 1992

[51] Int. Cl.⁵ .......................................... A61M 29/02
[52] U.S. Cl. ..................................... 604/101; 606/194
[58] Field of Search ............................... 604/96-103; 606/192-196; 600/18; 128/207.15

[56] References Cited

U.S. PATENT DOCUMENTS

| | | | |
|---|---|---|---|
| 2,849,001 | 8/1958 | Oddo | 604/101 |
| 3,045,677 | 7/1962 | Wallace | 604/101 |
| 4,484,579 | 11/1984 | Meno et al. | 604/101 X |
| 4,581,017 | 4/1986 | Sahota | 604/101 |
| 4,787,388 | 11/1988 | Hofmann | 606/194 |
| 4,878,495 | 11/1989 | Grayzel | 604/101 X |
| 4,906,244 | 3/1990 | Pinchuk et al. | 606/194 |
| 4,958,634 | 9/1990 | Jang | 606/194 |
| 4,994,033 | 2/1991 | Shockey et al. | 604/101 |
| 5,102,416 | 4/1992 | Rock | 606/194 |
| 5,179,961 | 1/1993 | Littleford et al. | 128/772 |

Primary Examiner—John D. Yasko
Assistant Examiner—Adam Cermak
Attorney, Agent, or Firm—Thomas R. Vigil

[57] ABSTRACT

An axial multi-chamber angioplasty balloon assembly for insertion into a blood vessel comprises a primary elongated, elastic, inflatable balloon having a first Young's Modulus, a distal portion, a proximal portion and an intermediate portion having a first diameter therebetween, defining a first chamber; a secondary elongated, elastic, inflatable balloon having a second Young's modulus, a distal portion, a proximal portion and an intermediate portion having a second diameter therebetween, defining a second chamber; the intermediate portions of the primary and the secondary balloons being attached in common; wherein the first and the second chambers define a variable dilation device for dilating an anatomical stricture having a first diameter-pressure characteristic curve defined by the primary balloon's Young's modulus, a second diameter-pressure characteristic curve defined by the secondary balloon's Young's modulus and a third diameter-pressure characteristic curve defined by the combined Young's modulus of the primary and secondary balloons.

18 Claims, 2 Drawing Sheets

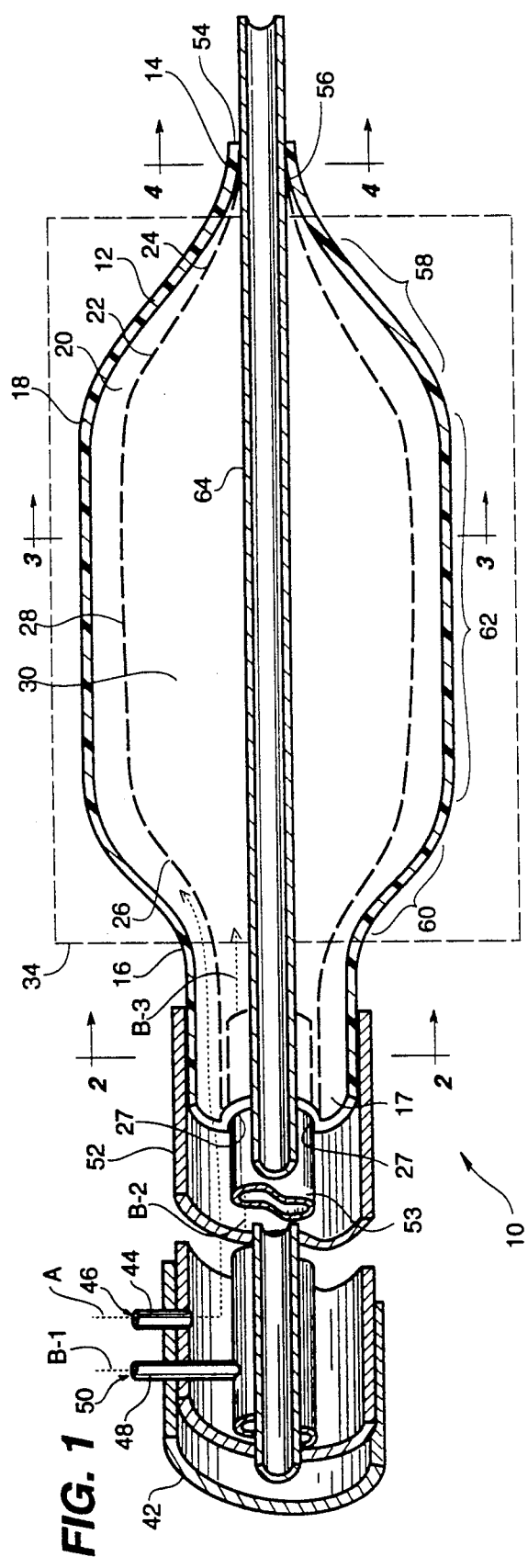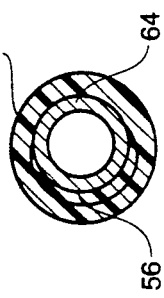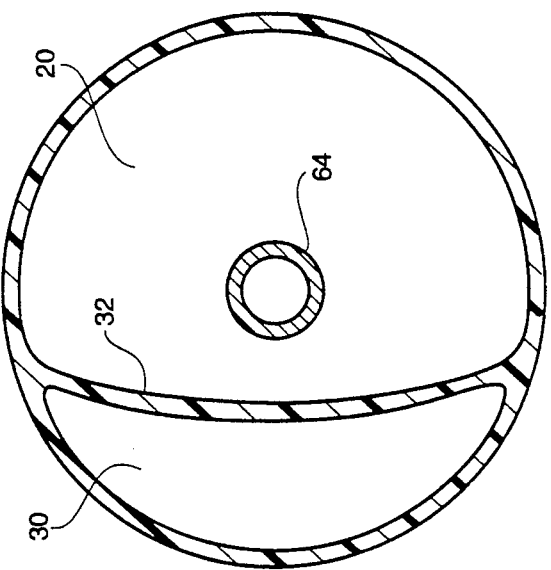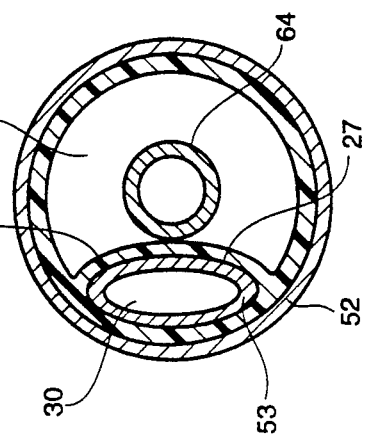

AXIAL MULTI-CHAMBER ANGIOPLASTY BALLOON ASSEMBLY

BACKGROUND OF THE INVENTION

1. Field of the Invention

This invention relates to dilatation balloon assemblies and particularly to a novel improvement in axial multi-chamber angioplasty balloon assemblies.

2. Description of the related art including information disclosed under 37 CFR §§1.97-1.99

Heretofore various angioplasty balloon assemblies have been proposed. Examples of such assemblies are disclosed in the following U.S. Patents:

| U.S. Pat. No. | Patentee |
| --- | --- |
| 3,045,677 | F. J. Wallace |
| 4,994,033 | Shockey, et al |

The Wallace U.S. Pat. No. 3,045,677, discloses a balloon catheter 10 adapted for insertion into a body cavity, such as a bladder, that includes two balloon portions integral with a catheter and having a tube 25 extending over the balloon portions and cemented at opposite ends 25A and 25B to a shaft 11 of the catheter 10.

The Shockey U.S. Pat. No. 4,994,033, discloses an intravascular drug delivery dilatation catheter including an inner expander member 30 and an outer expander member 22 having micropores 28 therethrough.

SUMMARY OF THE INVENTION

According to the present invention there is provided an axial multi-chamber angioplasty balloon assembly for insertion into a blood vessel comprising: a primary elongated, elastic, inflatable balloon having a first Young's Modulus, a distal portion, a proximal portion and an intermediate portion having a first diameter therebetween, defining a first chamber; a secondary elongated, elastic, inflatable balloon having a second Young's modulus, a distal portion, a proximal portion and an intermediate portion having a second diameter therebetween, defining a second chamber. The intermediate portions of the primary and the secondary balloons are attached in common. The first and said second chambers define a variable dilation device for dilating an anatomical stricture having a first diameter-pressure characteristic curve defined by the primary balloon's Young's modulus, a second diameter-pressure characteristic curve defined by the secondary balloon's Young's modulus and a third diameter-pressure characteristic curve defined by the combined Young's modulus of the primary and secondary balloons.

BRIEF DESCRIPTION OF THE DRAWINGS

FIG. 1 of the drawings is an axial longitudinal sectional view of an axial multi-chamber angioplasty balloon assembly in a partially dilated condition.

FIG. 2 of the drawings is a diametrical sectional view through the assembly in FIG. 1 and is taken along line 2—2 of FIG. 1.

FIG. 3 of the drawings is a diametrical sectional view of the assembly in FIG. 1 and is taken along line 3—3 of FIG. 1.

FIG. 4 of the drawings is a diametrical sectional view of FIG. 1 and is taken along line 4—4 of FIG. 1.

DESCRIPTION OF THE PREFERRED EMBODIMENT(S)

Figure 6:
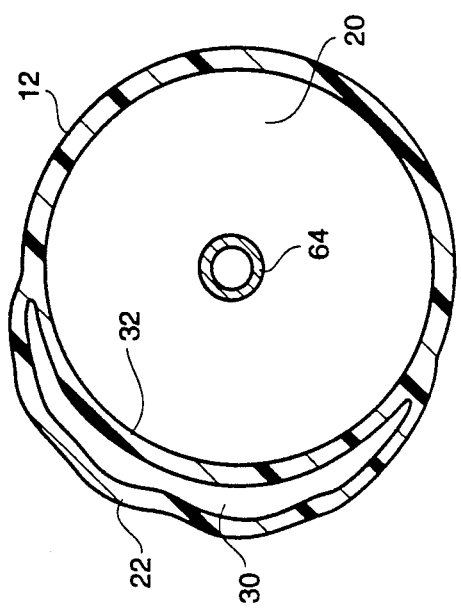
FIG. 6 of the drawings is a diametrical sectional view of the assembly in FIG. 1 and is taken along line 3—3 of FIG. 1, showing one balloon thereof in a dilated condition and the other in a partially dilated condition.

Referring now to the drawings in greater detail, illustrated in FIG. 1 is an axial multi-chamber angioplasty balloon assembly 10, for insertion into and dilation of an anatomical stricture in a blood vessel or other body cavity.

The multi-chamber balloon assembly 10 includes a primary elongated, inflatable balloon 12 having a distal portion 14, a proximal portion 16 and an intermediate portion 18 having a first diameter therebetween, defining a first chamber 20.

The assembly 10 further includes a secondary elongated, inflatable balloon 22 having a distal portion 24, a proximal portion 26 and an intermediate portion 28 having a second diameter therebetween, defining a second chamber 30. The intermediate portions 18 and 28 of the balloons 12 and 22 are attached or have a common junction point or area 32 extending longitudinally therebetween between the proximal portions 16 and 26 to the distal portions 14 and 24, respectively.

In FIG. 1, the assembly 10 further includes a variable dilation device 34 for dilating an anatomical stricture having a first linear diameter-pressure relationship or characteristic curve 36 defined by the primary balloon 12, a second linear diameter-pressure relationship or characteristic curve 38 defined by the secondary balloon 22 and a third linear diameter-pressure relationship or characteristic curve 40 defined by the combination or addition of the primary and secondary balloons 12 and 22.

Figure 7:
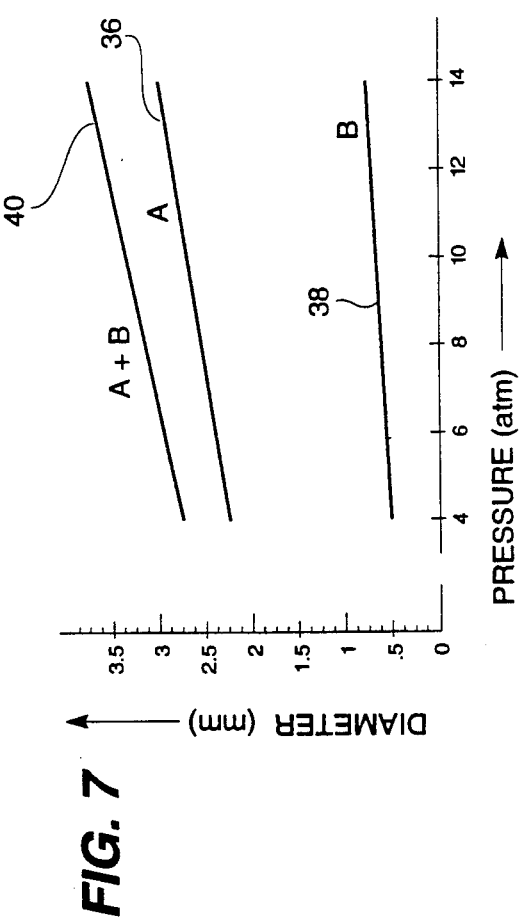
FIG. 7 of the drawings is a graph illustrating the predicted pressure and diameter characteristic curves or relationship of the balloon assembly of FIG. 1.

In one preferred embodiment, the balloons 12 and 22 are impermeate thereby having the predicted characteristics illustrated in FIG. 7, only having openings 17 and 27 for inflation thereof, respectively.

In use, the assembly 10 allows a physician, for example, to dilate an anatomical stricture with the use of the primary balloon 12 first characteristic curve 36 alone in FIG. 7, the secondary balloon 22 second characteristic curve 38 alone, or the combination of the primary and secondary balloons 12 and 22 third characteristic curve 40 for a larger diameter, without the need of withdrawing a narrow first mono-layer balloon assembly and reinserting a wider second balloon with all the inherent risks associated therewith. Stated another way, the assembly 10 allows a physician much more flexibility than mono-layer balloon assemblies.

In one preferred embodiment, the intermediate portion 18 of the primary balloon 12 includes a larger diameter than the intermediate portion 28 of the secondary balloon 22. The device 34 is designed to use primary balloon 12 to dilate a stricture first, and if not sufficient, the secondary balloon 22 is used to supplement the primary balloon 12.

In one preferred embodiment, the intermediate portion 18 of the primary balloon 12 includes a dilatation diameter of about 1.5 mm to about 3.5 mm for angioplasty end uses, and the intermediate portion 28 of the secondary balloon 22 includes a dilatation diameter of about 0.5 mm to about 1 mm, for a substantially uniform diameter along an elongate axis of device 34.

In one embodiment, the balloon assembly 10 further includes a hub 42 having a first member 44 with port 46 and a second member 48 having a port 50 for inflating the primary and secondary balloons 12 and 22, respectively, coupled to the proximal portions 16 and 26 of the balloons 12 and 22, by an outer and an inner intermediate placement sections 52 and 53. The assembly 10 further includes an inflating structure for inflating the balloons 12 and 22, respectively, connected to members 44 and 48 (not shown in the drawings).

In one preferred embodiment, the distal portions 14 and 24 are closed and include annular end portions 54 and 56, respectively, adhesively sealed or preferably heat sealed.

In FIG. 1, the variable dilation device 34 further includes a first inclined section 58, a second inclined section 60 and a middle section 62 therebetween comprising the combination of the primary and secondary balloons 12 and 22. The first inclined section 58 is axially-adjacent to the distal portions 14 and 24 of the balloons 12 and 22, and the second inclined section 60 is axially-adjacent to the proximal portions 16 and 26 of the balloons 12 and 22, respectively. In one embodiment, the first and second inclined sections 58 and 60 extend outwardly at an angle ranging from about 5° to about 85° when dilation device 34 is dilated, with respect to an axial or elongate axis through the center of the assembly 10 in FIG. 1, and preferably ranging from about 15° to 60°, and most preferably about 45° for a smooth and gradual increase and decrease in diameter of device 34, and for improved durability, flexibility and ease of insertion and removal of the variable dilation device 34.

Also, in one preferred embodiment, the balloon assembly 10 further includes a catheter 64. The catheter 64 is enclosed in the primary balloon 12 in alignment with an elongate axis for facilitating the insertion of the variable dilation device 34 in a body cavity.

In one preferred embodiment, the intermediate placement sections 52 and 53 provide two dashed paths identified as A and B-1, B-2 and B-3, from the ports 46 and 50 of first and second members 44 and 48, respectively, for inflating or dilating the balloons 12 and 22. The paths A and B provide a means for delivery of dilation fluid, to device 34 primary and secondary balloons 12 and 22, respectively.

In FIG. 7, the variable dilation device 34 predicted diameter and pressure relationship or graph is illustrated. The graph includes a first linear diameter-pressure relationship curve 36, a second linear diameter-pressure relationship curve 38, and a third linear diameter-pressure relationship curve 40. The first diameter-pressure characteristic curve 36 relates to a condition when the primary balloon 12 is being inflated and the secondary balloon 22 is not inflated, as shown in FIG. 6. The second linear diameter-pressure relationship curve 38 relates to a condition when only the secondary balloon 22 is inflated, such as may be indicated in FIG. 2.

The third diameter-pressure relationship curve 40, in FIG. 7, corresponds to the drawing in FIG. 3, wherein both the primary and secondary balloons 12 and 22 are fully inflated. If plotted on a third characteristic curve 40 in FIG. 7, it would correspond to a point on the characteristic curve 40 near the top and to the right on such line. If the drawing in FIG. 6 were plotted on the characteristic curve 40, it would be to the left and below the just stated point in FIG. 7.

Figure 5:
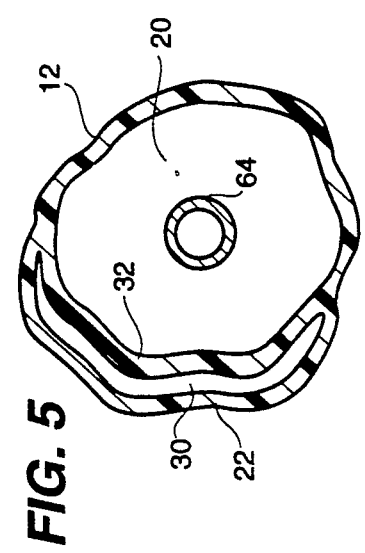
FIG. 5 of the drawings is a diametrical sectional view of the assembly in FIG. 1, showing both balloons thereof in a partially dilated condition.

The drawing in FIG. 5 corresponds to a point on the third characteristic curve 40 near the bottom and to the left on the graph of FIG. 7.

As can be seen in FIG. 7, each characteristic 36, 38 and 40 travels linearly, so if there is an increase in pressure, the diameter increases incrementally. In FIG. 7, characteristic curves 36, 38 and 40 are not parallel, but can be if desired. These characteristics are dependent on the modulus of elasticity of the balloons 12 and 22.

In use, the assembly 10 allows a physician, for example, to dilate an anatomical stricture with the use of the primary balloon 12 having the first characteristic curve 36 alone in FIG. 7, the secondary balloon 22 having the second characteristic curve 38 alone, or the combination of the primary and secondary balloons 12 and 22 having the third characteristic curve 40 for a larger diameter, without the need of withdrawing a narrow first mono-layer balloon assembly and reinserting a wider second balloon with all the inherent risks associated therewith. Stated another way, the assembly 10 allows a physician much more flexibility than mono-layer balloon assemblies.

For example, mono-layer balloon assemblies are known which have distention properties which are not variable and behave similar to those in the first or second characteristic curve 36 or 40, alone the entire range in FIG. 7. In such mono-layer assemblies, it is possible to obtain dimensional variability only with an undesirable increase in size beyond a desired or safe working pressure range. In contrast, the assembly 10 provides a clinician the opportunity to increase the diameter of variable dilation device 34, by inflating the primary balloon 12 alone, the secondary balloon 22 alone, or the combination of the primary and secondary balloons 12 and 22. Advantageously, the assembly 10 provides a clinician with the ability to vary the inflated variable dilation device 34 diameter within a safe working pressure range, and further allows a pressure increase with a size increase, that is safer than a conventional mono-layer balloon, resulting in improved substantially uniform circumferential pressure and improved dilation of a stricture within an area of stenosis, for example. Further, the assembly 10 provides the benefit of eliminating the need to change to a second catheter assembly with a larger balloon diameter when a larger dilating diameter is required.

The assembly 10 can be used for many types of dilation products, such as angioplasty, valvuloplasty, urethroplasty, salpingoplasty and the like. The assembly 10 can be attached to an over the wire, fixed wire, hybrid over the wire or rapid exchange monorail type dilation system. The assembly 10 is particularly suited for dilating blood vessels within an area of stenosis.

The assembly 10 can also be used to deploy a stent in a blood vessel or body cavity (not show in the drawings). The stent is received around the assembly 10 variable dilation device 34, and the entire device 34 and stent is received within the body cavity. When assembly 10 is used in conjunction with a stent, the balloons 12 and 22 exert radially, outwardly pressure to and against a stent, to expand the stent as designed against an appropriate body cavity. After the stent has been deployed, the device 34 is deflated and removed.

In one embodiment, the balloons 12 and 22 are tubular, annular, flexible and expandable and comprise a polymeric material.

In one embodiment, the catheter is aligned longitudinally in the secondary balloon.

In one preferred embodiment, the balloons 12 and 22 comprise at least one polymeric material selected from the group consisting of polyolefins, copolymers of polyolefins, polyamides, polyvinyl chloride and polyethylene terephthalate, and combinations and permutations thereof, and more preferably a polyamide such as nylon because of its desirable properties, such as elasticity, durability, formability, manufacturability, etc. In one embodiment, the balloons 12 and 22 comprise a polyamide such as 70D nylon or 75D nylon for desired properties. In one preferred embodiment, both balloons 12 and 22 comprise the same polymeric material of 75D nylon. See for example, U.S. Pat. Nos. 5,108,415 and 4,906,244 which disclose nylon balloon assemblies and methods of making same.

The primary and secondary balloons 12 and 22 include a Young's modulus, which can range widely. In one embodiment, the Young's modulus of the primary balloon 12 causes the primary balloon to expand at a rate of about 1%/atmosphere (atm) to about 3%/atm and typically at about 1.5%/atm. Similarly, the secondary balloon 22 Young's modulus can range widely. Preferably, it causes the secondary balloon to expand at a rate of about 1%/atm to about 3%/atm, and typically at about 1.5%/atm.

In one preferred embodiment, the Young's modulus of balloons 12 and 22 is the same.

The length of the variable dilation device 34 can range widely depending on the intended application. In one embodiment, the length ranges from about 50 mm to about 10 mm, preferably from about 30 mm to about 10 mm and typically about 20 mm for angioplasty dilation products. Similarly, the diameter of device 34 can range widely depending on the intended application, preferably the diameter ranges from about 30 mm to about 1 mm and more preferably from about 5 mm to about 1 mm in diameter when used as an angioplasty dilation product.

The primary and secondary balloons 12 and 22 each have wall thicknesses that can vary widely depending on the material used. In one embodiment, each balloon 12 and 22 has a wall thickness of about 2 mils or less, preferably about 1 mil or less when utilizing a polymeric material such as a polyamide. One preferred material is a polyamide, for elasticity, durability, strength and minimal volume and surface area for ease of insertion and withdrawal into and out of body cavity.

In use, a physician utilizing the dilation device 34 follows the following procedure. First, the physician inserts dilation device 34 about the stricture to be dilated. A catheter can be utilized to help expedite this procedure, if desired. Second, he or she dilates a blood vessel by inflating the primary and/or secondary balloons 12 and 22, either individually or simultaneously, as in FIG. 7. In one preferred embodiment, the primary balloon 12 can be inflated alone, to obtain the first characteristic 36 in FIG. 7. If the diameter of the primary balloon of device 34 is not wide enough, the physician can further increase the diameter of device 34 as illustrated in FIG. 3, by inflating the secondary balloon 22 to obtain the third characteristics 40 in FIG. 7. Alternatively, both balloons 12 and 22 can be inflated simultaneously. Therefore, the dilation device 34 is deflated and removed. The dilation device 34 provides a physician much flexibility with respect to dilation diameter in an area of stenosis. The assembly 10 is resistant to rupture and provides a smooth circumferential radial-pressure to the stricture being dilated.

Although only one embodiment of this invention has been shown and described, it is to be understood that modifications and substitutions, as well as rearrangements and combinations of the preceding embodiment can be made by those skilled in the art without departing from the teachings of this invention. Accordingly, the scope of the invention is only to be limited as necessitated by the accompanying claims.

I claim:

1. An axial multi-chamber angioplasty balloon assembly for insertion into a blood vessel comprising:
   a primary elongated, elastic, inflatable balloon having a first Young's Modulus, a distal portion, a proximal portion and an intermediate portion having a first diameter therebetween, defining a first chamber;
   a secondary elongated, elastic, inflatable balloon having a second Young's modulus, a distal portion, a proximal portion and an intermediate portion having a second diameter therebetween, defining a second chamber; said intermediate portions of the primary and the secondary balloons being attached in common;
   said first and said second chambers defining a variable dilation device for dilating an anatomical stricture having a first diameter-pressure characteristic curve defined by said primary balloon's Young's modulus, a second diameter-pressure characteristic curve defined by said secondary balloon's Young's modulus and a third diameter-pressure characteristic curve defined by a combined Young's modulus of said primary and secondary balloons.

2. The assembly of claim 1, wherein said primary and secondary balloons are flexible and expandable.

3. The assembly of claim 1, wherein said primary and secondary balloons comprise a polymeric material.

4. The assembly of claim 1, wherein said primary balloon and said secondary balloon comprise at least one polymeric material selected from the group consisting of polyolefins, copolymers of polyolefins, polyamides, polyvinyl chloride and polyethylene terephthalate.

5. The assembly of claim 1, further comprising a catheter aligned longitudinally in the primary or secondary balloon.

6. The assembly of claim 1, wherein said diameter of the primary balloon is greater than the diameter of the secondary balloon.

7. The assembly of claim 1, wherein said primary and secondary balloons have a rate of radial expansion ranging from about 1%/atm to about 3%/atm.

8. The assembly of claim 1, wherein said primary and secondary balloons include a substantially uniform wall thickness throughout.

9. The assembly of claim 8, wherein said wall thickness is about 2 mils or less.

10. The assembly of claim 1, wherein said dilation device includes a dilation diameter of about 5 mm to about 1 mm.

11. The assembly of claim 1, further comprising a molded hub section having a first port for inflating the primary balloon and a second port for inflating the secondary balloon, coupled to said proximal portions of the primary and the secondary balloons.

12. The assembly of claim 1, wherein said dilation device includes a substantially uniform diameter along an elongate axis thereof.

13. The assembly of claim 1, wherein the assembly includes a length comprising a distance from the proximal to the distal portion thereof of about 50 mm or less, and a dilatation diameter of about 30 mm or less, at a pressure ranging from 1 atm to about 20 atm.

14. The assembly of claim 1, wherein said primary and secondary balloons are substantially impermeate having dilation ports.

15. The assembly of claim 1, wherein said intermediate portions of the primary and the secondary balloons are attached to each other between the distal portion and proximal portion thereof.

16. The assembly of claim 1, further comprising means for inflating said primary and secondary balloons.

17. The assembly of claim 1, further comprising a hub and an outer intermediate placement section, said outer intermediate placement section attached circumferentially to and within said hub at a proximal end and being attached to and around said proximal portion of said primary balloon at the other end.

18. The assembly of claim 1, further comprising a hub and an inner intermediate placement section and an outer intermediate placement section, said inner intermediate placement section being coupled to said hub at a proximal end and attached to and circumferentially with the proximal portion of the secondary balloon at the other distal end thereof.

* * * * *